(12) United States Patent
Gevers

(10) Patent No.: US 10,677,745 B2
(45) Date of Patent: Jun. 9, 2020

(54) TOMOGRAPHY DEVICE FOR ELECTRICAL IMPEDANCE TOMOGRAPHY

(71) Applicant: KROHNE Messtechnik GmbH, Duisburg (DE)

(72) Inventor: Martin Gevers, Bochum (DE)

(73) Assignee: KROHNE Messtechnik GmbH, Duisburg (DE)

( * ) Notice: Subject to any disclaimer, the term of this patent is extended or adjusted under 35 U.S.C. 154(b) by 0 days.

(21) Appl. No.: 16/149,798

(22) Filed: Oct. 2, 2018

(65) Prior Publication Data
US 2019/0101500 A1    Apr. 4, 2019

(30) Foreign Application Priority Data

Oct. 4, 2017    (DE) .......................... 10 2017 123 032

(51) Int. Cl.
*G01N 27/02*    (2006.01)
*G01N 33/28*    (2006.01)

(52) U.S. Cl.
CPC ........... *G01N 27/026* (2013.01); *G01N 33/28* (2013.01)

(58) Field of Classification Search
CPC ...... G01N 27/026; G01N 33/28; G08B 17/06; G08B 17/00; G08B 25/002; G08B 17/12; G08B 21/185; H02H 1/0015
See application file for complete search history.

(56) References Cited

U.S. PATENT DOCUMENTS

| | | | | |
|---|---|---|---|---|
| 2010/0007357 | A1* | 1/2010 | Ammari | A61B 5/0536 324/649 |
| 2011/0017062 | A1* | 1/2011 | DiLeo | B01D 35/143 95/22 |
| 2012/0223717 | A1 | 9/2012 | LaBrecque | |
| 2014/0184249 | A1 | 7/2014 | Saafi et al. | |
| 2014/0320130 | A1* | 10/2014 | Nistler | G01R 33/3642 324/322 |
| 2014/0365009 | A1* | 12/2014 | Wettels | B25J 9/1612 700/258 |
| 2015/0092642 | A1* | 4/2015 | Geboff | H04L 69/329 370/311 |
| 2015/0297099 | A1* | 10/2015 | Arad (Abboud) | A61B 5/686 600/375 |

(Continued)

*Primary Examiner* — Christopher P McAndrew
*Assistant Examiner* — Zannatul Ferdous
(74) *Attorney, Agent, or Firm* — Whitmyer IP Group LLC

(57) ABSTRACT

A tomography device for electric impedance tomography in a measuring volume having at least two measuring ports. The object is to provide a tomography device that allows adaptation to an application with less effort and/or a greater number of measuring ports than the prior art. The object is achieved with a tomography device in that the tomography device has at least two measuring modules, that each of the measuring modules is designed to be controllable via the respective module radio device and module control device and, in each case has a module control device, a module radio device and one of the measuring ports, and the respective measuring port can be arranged at a freely selectable position on a perimeter of the measuring volume, and that each of the module control devices is designed to carry out measurements for electrical impedance tomography using the respective measuring port.

12 Claims, 2 Drawing Sheets

(56) References Cited

U.S. PATENT DOCUMENTS

2015/0308869 A1* 10/2015 Black .................. G01N 29/036
                                                    73/861.04
2016/0103085 A1    4/2016 Mehregany
2017/0296059 A1   10/2017 Anderson

* cited by examiner

TOMOGRAPHY DEVICE FOR ELECTRICAL IMPEDANCE TOMOGRAPHY

TECHNICAL FIELD

The invention concerns a tomography device for electrical impedance tomography in a measuring volume with at least two measuring ports.

BACKGROUND

Electrical impedance tomography provides a spatially resolved analysis of electrical properties, such as permittivity and conductivity, of a multi-phase medium in a measuring volume, wherein the medium can also flow through the measuring volume. The result of a spatially resolved analysis of a flowing multi-phase medium, for example, is a spatial visualization of the individual phases of the medium in the measuring volume. A spatially resolved analysis first requires the determination of a spatial distribution of an electrical property in the measuring volume. To determine this, a tomography device for electrical impedance tomography has at least two measuring ports and a control device. Measuring ports are basically arranged at a perimeter of the measuring volume. A measuring port comprises at least one measuring electrode which is designed for coupling electrical excitation signals into a medium and for decoupling an electrical measuring signal from a medium which has been caused by an excitation signal in the medium. In most cases, however, a measuring port has two measuring electrodes. A spatial distribution of an electrical property is determined by the control device, for example, generating excitation signals, coupling them alternately into the medium with one of the measuring ports, decoupling measuring signals from the medium caused by the excitation signals with the other measuring port or, if the tomography device comprises more than two measuring ports, with the other measuring ports, and determining the spatial distribution of the electrical property from the excitation signals and the measuring signals.

Tomography devices for electrical impedance tomography are suitable for applications in the extraction of crude oil and in process technology, especially in the chemical industry. Petroleum is a multi-phase medium having the phases oil, gas and water, which flows at high speed during extraction. For example, generic tomography devices provide spatial visualization of the individual phases of oil in real time. In process technology, one application is the control of mixing and separating processes, for example.

Tomography devices for electrical impedance tomography known from the prior art have electrical cables for connecting measuring ports and control devices. Due to the electrical cables and the plug connections required for them at the control devices, the number of measuring ports is limited and the adaptation of a generic tomography device to an application is complex. Furthermore, often necessary long cables lead to measurement errors due to parasitic capacitances and inductances associated with their length. In many cases, amplifiers must also be integrated into long cables, which further complicates adaptation.

SUMMARY

One object of the present invention is, thus, to provide a tomography device of the type described, which allows adaptation to an application with less effort and/or a greater number of measuring ports.

In the case of a tomography device for electrical impedance measurement of the type described, the task is achieved by the features of patent claim 1. The tomography device has at least two measuring modules. Each of the measuring modules has a module control device, a module radio device and one of the measuring ports. The measuring modules are designed to be controllable via the respective module radio device and module control device and the respective measuring port can be arranged at a freely selectable position on a perimeter of the measuring volume. The module control devices are designed to perform measurements for electrical impedance tomography using the respective measuring port.

Accordingly, a measuring module also enables a spatially separate arrangement of module control device, module radio device and measuring port. If the module control device and the module radio device, on the one hand, and the measuring port, on the other hand, are separate, a plug connection between the two is a suitable solution. However, such a measuring module preferably has a measuring module housing, wherein the module control device, the module radio device and the measuring port of the measuring module are arranged in the measuring module housing. The controllability of a measuring module via its module radio device and module control device comprises, in particular, the control of measurements for electrical impedance tomography by this measuring module.

The measuring volume is limited by the perimeter. If, for example, a medium flows through a measuring tube, a section of the measuring tube is part of the perimeter. The arrangement of the measuring modules or the measuring ports of the tomography device on the perimeter is then carried out by arrangement on the measuring tube and determines the section of the measuring tube which is part of the perimeter. The positions of the measuring modules or measuring ports are freely selectable to the extent that the positions are suitable for carrying out measurements. Tomography devices are basically those for electrical impedance tomography and measurements are basically measurements for electrical impedance tomography.

The tomography device according to the invention has various advantages over the prior art. By replacing the use of electrical cables for connecting measuring ports and control devices with module radio devices, a greater number of measuring ports, in particular, is enabled and the effort required for adaptation to an application is reduced. The number of measuring ports, i.e. the measuring modules, can be increased in many applications, since the electrical cables requiring space can be eliminated, such space not being available in many applications and in this manner limiting the number of measuring ports. In addition, the limited number of existing electrical connections to control devices required for the cables is often the limit for the number of measuring ports in the prior art. The effort for adaptation to an application is reduced in particular in that the arrangement of measuring modules at the perimeter of a measuring volume is simplified due to the elimination of the arrangement of the electrical cables.

It is provided in one design of the tomography device according to the invention that the module radio device implements a Bluetooth or WLAN standard which implements the synchronization of time bases. Preferably, a WLAN standard with TimeSync is implemented. By synchronizing time bases in the measuring modules, the effects of latencies in communication channels can be compensated. Latency is a temporally fluctuating delay that occurs when data is transmitted over a communication channel. Synchronized time bases ensure synchronous measurements, so that latencies in communication channels have no negative influence on the measurements.

In a further design, it is provided that the tomography device has a central control device and a central radio device. The central radio device and the module radio devices are each designed to establish a communication channel between the central radio device and one of the module radio devices. Furthermore, the central control device is designed for the control and evaluation of measurements. Preferably, the central control device and the central radio device are arranged separately from the measuring modules. For example, they are arranged in a common housing. Preferably, not only the module radio devices but also the central radio device implements a Bluetooth or a WLAN standard, in particular a WLAN standard with TimeSync. The communication channels thus replace the electrical cables between the central control device and the measuring ports. The communication channels are bidirectional. This means that data can be transmitted from the central control device to any of the measuring modules as well as from any of the measuring modules to the central control device.

Measurements for electrical impedance tomography comprise, in particular, those for determining the spatial distribution of an electrical property in the measuring volume. In these measurements, excitation signals from one measuring module are coupled into a medium and measurement signals generated by the excitation signals in the medium are decoupled from the other measuring module or, if there are more than two measuring modules, from the other measuring modules. The voltages and/or currents of the excitation signals and/or the measurement signals are determined by the tomography device, for example the central control device or the module control devices, according to magnitude and/or phase. Thus, a sufficiently accurate synchronization of the time bases of the individual measuring modules is necessary, since otherwise the temporal coherence of an excitation signal and the measuring signals caused by the excitation signal would be impaired. Consequently, the accuracy of a spatially resolved analysis would also be impaired. Synchronization is sufficiently accurate if the impairment of a spatially resolved analysis in an application is still acceptable. A measure for a still acceptable inaccuracy of the synchronization in an application is the frequencies of the excitation and measuring signals provided in the application. Preferably the frequencies are in the range between 100 kHz and 10 MHz.

In a further design of the tomography device, it is provided that the module radio devices are designed to establish communication channels between one another. The above explanations in respect to the synchronization of time bases and thus of measurements apply accordingly. This design can be provided as an alternative or in addition to the above design.

If this design is additionally provided, then there are not only communication channels between the central radio device and the individual module radio devices, but there are also communication channels between the module radio devices themselves. If this design is provided as an alternative, then communication channels only exist between the module radio devices themselves. In a design based on this design, it is then provided that the measuring modules are designed as a self-organizing network via the communication channels and for controlling and evaluating measurements. The module control devices then take over the functionality of the central control device. The functionality is, for example, transferred to a single module control device or distributed among several module control devices.

If the module radio devices are designed to establish communication channels between themselves, it is advantageous if the measuring modules are designed to transmit data from one of the measuring modules via one of the communication channels to another one of the measuring modules. Due to the configuration for transferring data among one another, the measuring modules can assume different tasks of the central control device.

In a further design of the tomography device, it is provided that at least two of the measuring modules are identically designed. The identical design of the measuring modules reduces their manufacturing costs due to higher quantities and enables further modularization of the tomography device, since identically designed measuring modules must have all the functions of the various different measuring modules previously used.

In a further design, it is provided that at least one of the measuring ports is designed to be in galvanic or capacitive contact with a medium in the measuring volume. In the case of a galvanic contact, at least one measuring electrode of a measuring port is in direct contact with a medium. With a capacitive contact, there is an interface between the at least one measuring electrode and a medium, which also acts as a dielectric. Preferably, the module control devices are designed for both a galvanic and a capacitive contact.

It is provided in a further design that the tomography device has a cloud memory and that the cloud memory is designed for management of data. This enables decentralized storage of data, such as the data reproducing the measurement signals.

The above versions usually only deal with two measuring modules. However, these versions apply analogously to any number of measuring modules.

BRIEF DESCRIPTION OF THE DRAWINGS

In detail, there is a plurality of possibilities for designing and further developing the tomography device. For this, reference is made both to the patent claims subordinate to patent claim 1 and to the following description of a preferred embodiment in conjunction with the drawing. The drawing shows FIG. 1 provides an embodiment of a tomography device in a partially perspective view.

DETAILED DESCRIPTION

Figure 1:
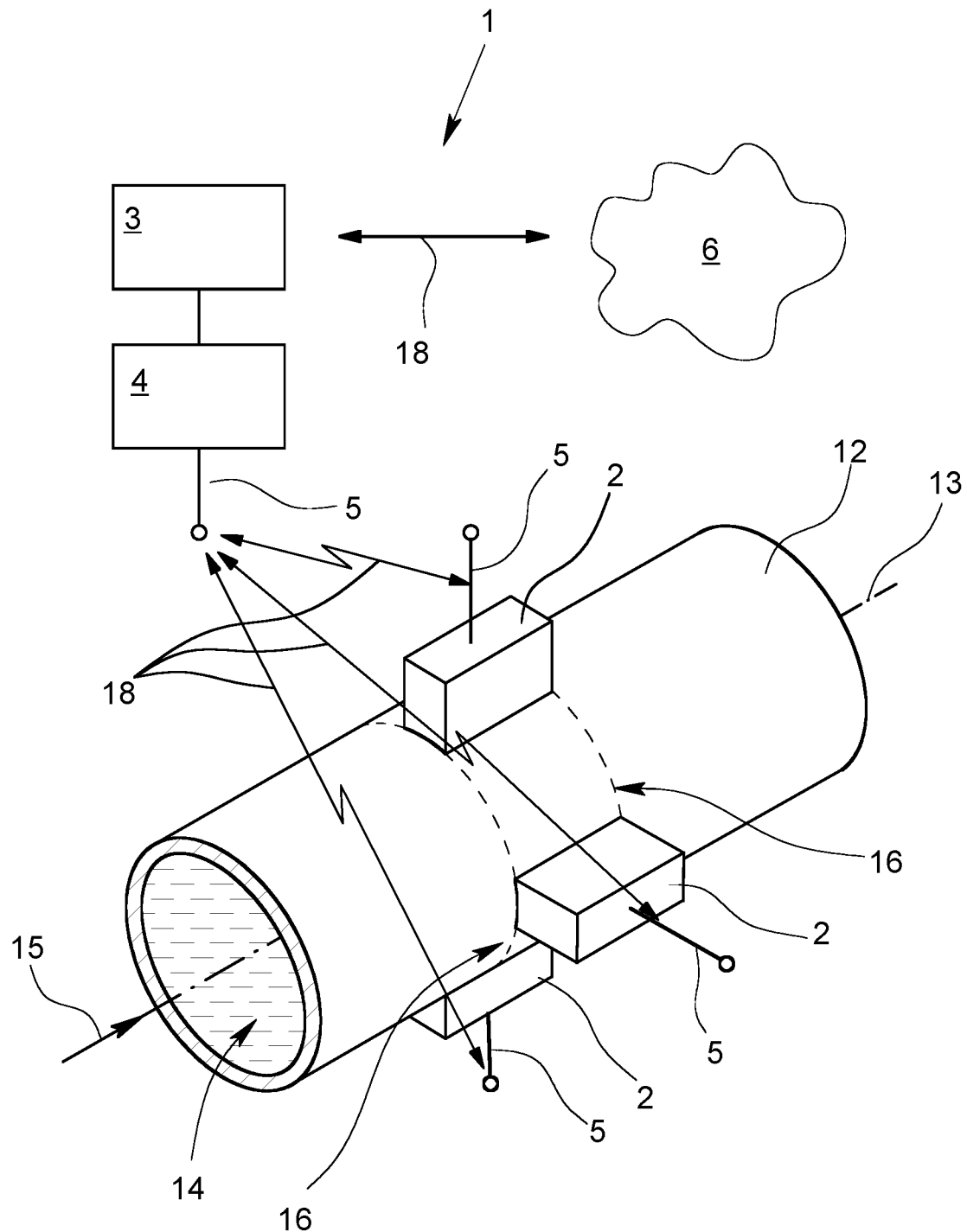
Figure 2:
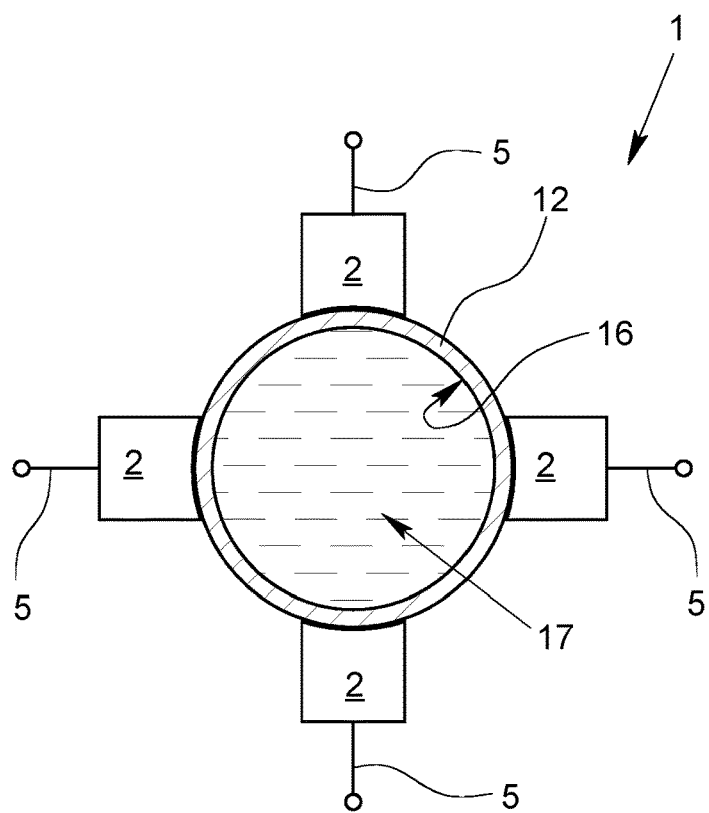
FIG. 2 illustrates the embodiment in a front view and FIG. 3 illustrates an section of the embodiment in a sectional front view.

FIG. 1 shows in an abstracted partially perspective representation and FIG. 2 in an abstracted front view essential features of an embodiment of a tomography device 1 for electrical impedance tomography. The tomography device 1 has four measuring modules 2, a central control device 3, a central radio device 4, an antenna 5 and a cloud memory 6.

Figure 3:
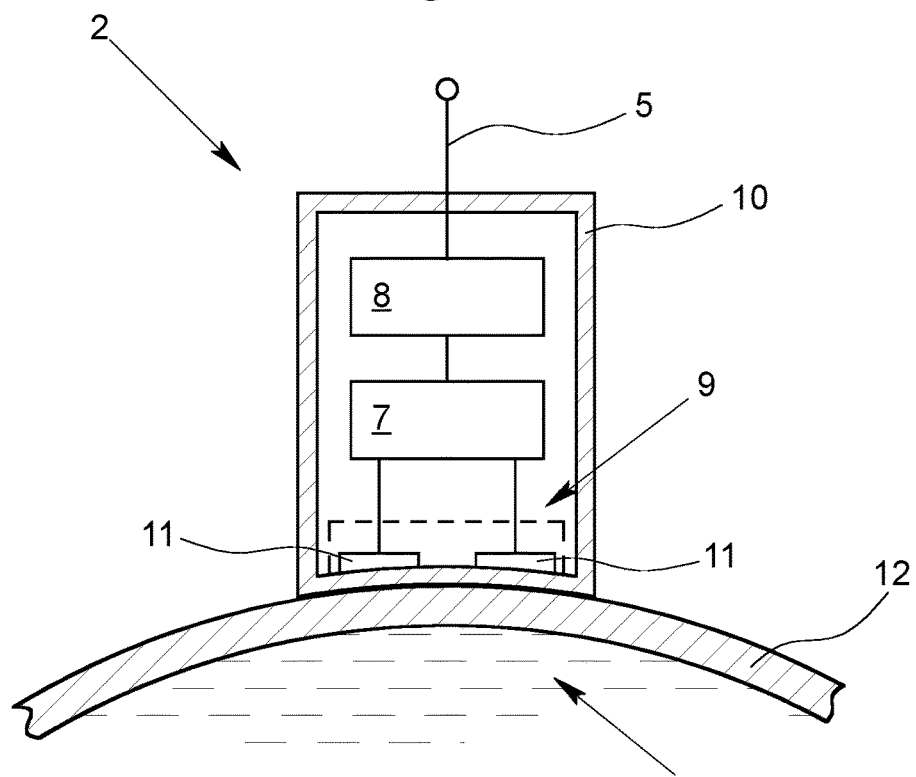

FIG. 3 shows the essential features of one of the four measuring modules 2 in a sectional front view, wherein all measuring modules 2 are identical. The measuring module 2 has a module control device 7, a module radio device 8, an antenna 5, a measuring port 9 and a measuring module housing 10. The measuring port 9 has two measuring electrodes 11. The module control device 7, the module radio device 8 and the measuring port 9 having the two measuring electrodes 11 are arranged in the measuring module housing 10, whereas the antenna 5 is arranged outside the measuring module housing 10. The module control device 7 is electrically connected to the module radio device 8 on the one hand and to the measuring electrodes 11 of the measuring port 9 on the other hand. The module radio device 8 is also electrically conductively connected to the antenna 5. The measuring module 2 is designed to be controllable via the module radio device 8 and module control device 7. The module control device 7 is designed to carry out measurements for electrical impedance tomography using the measuring port 9.

The measuring modules 2 are arranged at freely selected positions on a measuring tube 12, see FIGS. 1 and 2. In an alternative configuration, the measuring ports 9 are arranged separately from the module control devices 7 and module radio devices 8 and on the measuring tube 12. With this design, the arrangement of the measuring ports 9 is preferably already carried out during the production of the measuring tube 12, so that the production of the tomography device 1 is simplified. The module control devices 7 and module radio devices 8 in the measuring module housing 10 and the measuring ports 9 are then electrically connected with plug connectors.

The measuring tube 12 has a measuring tube longitudinal axis 13 and a multi-phase medium 14 flows through it in the flow direction 15. The measuring tube 12 and the measuring electrodes 11 of the measuring modules 2 together form a perimeter 16 of a measuring volume 17. The inner wall of the measuring tube 12 forms the perimeter 16 of the measuring volume 17 in a direction radial to the measuring tube longitudinal axis 13 and the extension of the measuring electrodes 11 in a direction axial to the measuring tube longitudinal axis 13 forms the perimeter 16 of the measuring volume 17 in a direction axial to the measuring tube longitudinal axis 13. The measuring electrodes 11 of the measuring ports 9 are capacitively coupled with the medium 14, wherein the wall of the measuring tube 13 acts as a dielectric.

The central radio device 4 and the module radio devices 8 are each designed to establish a communication channel 18 between the central radio device 4 and one of the module radio devices 8. The communication channels 18 between the central radio device 4 and the module radio devices 8 do not have a physical medium for the transmission of data. To compensate for the effect of the latency of the communication channels 18, so that sufficient synchronization of the measurements with the measuring modules 2 is ensured, the central radio device 4 and the module radio devices 8 are designed in accordance with a WLAN standard with Time-Sync. Since the frequencies of the excitation and measuring signals are in the range between 100 kHz and 10 MHz, sufficient synchronization of the time bases of the measurement modules 2 is ensured.

The central control device 3 and the cloud memory 6 are connected to one another via a further communication channel 18. This communication channel 18 can also be free of a physical medium. The cloud memory 6 is designed for management of data, which is determined in particular by the measurement modules 2 during measurement. This data includes, in particular, excitation and measuring signals and the results of spatially resolved analyses.

The invention claimed is:

1. A tomography device for electrical impedance tomography of a multi-phase medium flowing through a measuring volume, comprising:

at least two measuring ports; and
at least two measuring modules;
wherein each of the measuring modules has a module control device, a module radio device and one of the measuring ports;
wherein each of the measuring modules is designed to be controllable via the respective module radio device and module control device;
wherein the respective measuring port is arranged at a freely selectable position on a perimeter of the measuring volume; and
wherein each of the module control devices is designed to carry out measurements for the electrical impedance tomography using the respective measuring port.

2. The tomography device according to claim 1, wherein the module radio devices implement a Bluetooth or a WLAN standard with TimeSync, which implements the synchronization of time bases.

3. The tomography device according to claim 1, wherein the tomography device has a central control device and a central radio device;
wherein the central radio device and the module radio devices are designed in each case to establish a communication channel between the central radio device and one of the module radio devices; and
wherein the central control device is designed to control and evaluate measurements.

4. The tomography device according to claim 1, wherein the module radio devices are designed to establish communication channels with one another.

5. The tomography device according to claim 4, wherein the measuring modules are designed as a self-organizing network via the communication channels and for controlling and evaluating measurements.

6. The tomography device according to claim 4, wherein the measuring modules are designed to transmit data from one of the measuring modules to another one of the measuring modules via one of the communication channels.

7. The tomography device according to claim 1, wherein at least two of the measuring modules are identical.

8. The tomography device according to claim 1, wherein at least one of the measuring ports is designed to be in galvanic or capacitive contact with a medium in the measuring volume.

9. The tomography device according to claim 1, wherein the tomography device has a cloud memory and the cloud memory is designed to manage data.

10. The tomography device according to claim 1, wherein the electrical impedance tomography provides a spatial visualization of individual phases of the multi-phase medium flowing through the measuring volume.

11. The tomography device according to claim 1, wherein each of the module control devices includes at least one measuring electrode for coupling an electrical excitation signal into the multi-phase medium and for decoupling a resulting electrical measuring signal from the multi-phase medium.

12. The tomography device according to claim 1, wherein each of the module control devices includes at least two electrodes configured to be capacitively coupled with the multi-phase medium flowing through the measuring volume.

* * * * *